(12) United States Patent
Al Azemi

(10) Patent No.: US 8,815,164 B1
(45) Date of Patent: Aug. 26, 2014

(54) PORTABLE CENSER BAG

(71) Applicant: Wasmeyyah Mas Al Azemi, Sabah Al Salem (KW)

(72) Inventor: Wasmeyyah Mas Al Azemi, Sabah Al Salem (KW)

( * ) Notice: Subject to any disclaimer, the term of this patent is extended or adjusted under 35 U.S.C. 154(b) by 0 days.

(21) Appl. No.: 13/956,391

(22) Filed: Aug. 1, 2013

(51) Int. Cl.
*A61L 9/02* (2006.01)
*A61L 9/03* (2006.01)

(52) U.S. Cl.
CPC ... *A61L 9/03* (2013.01); *A61L 9/02* (2013.01); *A61L 9/032* (2013.01)
USPC ............ 422/125; 422/120; 422/124; 422/126

(58) Field of Classification Search
USPC .................................. 422/4, 5, 120, 123–126
See application file for complete search history.

(56) References Cited

U.S. PATENT DOCUMENTS

| 3,058,178 | A | 10/1962 | Campagna |
| 4,198,375 | A | 4/1980 | Rogers |
| 6,619,768 | B1 * | 9/2003 | Northrop et al. ............... 312/290 |
| 8,435,451 | B2 * | 5/2013 | Al-Mahnna ................... 422/126 |

* cited by examiner

*Primary Examiner* — Sean E Conley

(57) ABSTRACT

The present invention relates generally Portable censer bag, where the censer elements are mounted inside the said bag. The portable bag is designed to mount all censer elements inside, so we can take it everywhere and use it easily. The censer bag is power by electric power supply 220 v AC and also, with rechargeable battery 12 v DC through the adapter. Every piece of the censer mounted in a suitable place in the bag according to its size or height. And so, each piece is fixed while carrying the bag. There is a decoration lighting strip surround the bag which also used as indication of the charging of the battery according to light intensity. The Bag made of strong materials to withstand the shocks and coated with a layer of sponge and an artificial skin.

9 Claims, 5 Drawing Sheets

PORTABLE CENSER BAG

BACKGROUND OF THE INVENTION

1. Field of the Invention

The present invention relates generally Portable censer bag shaped like a conventional suitcase with handle, where the censer elements are housed inside the said bag.

2. Description of the Related Art

Incense burners are well known and have been in use for many years. Burners of various designs are appropriate for different applications ranging from religious services to a device for killing flying insects and/or dispensing a pleasant aroma.

For example, a U.S. Pat. No. 3,058,178 of Campagna relates to a portable incense burner that is particularly well suited for use in religious ceremonies. Early burners placed burning charcoals in a portable receptacle provided with holes in the wall to permit air to pass to the charcoal to keep it burning and to permit the escape of incensed fumes. Incense is placed over the burning coal to produce the fumes. In order to overcome a problem associated with receptacles becoming very hot on the outer surface, and the inconvenience of refilling at an inconvenient time. Campagna teaches the use of an electrical socket and a thermostat to control the heat applied to the incense.

A more recent patent Rogers, U.S. Pat. No. 4,198,375 discloses an incense burner consisting of an exterior receptacle fitted with an ash collecting basket and supporting a cigarette lighter within the receptacle together with an axially disposed spindle. A disc having a plurality of circumferentially disposed holes dimensioned to accept sticks of incense is supplied on the spindle above the receptacle and a wire meshed cap is fitted over the disc at the top of the receptacle. The disc can be rotated to permit selective ignition of one or more incense sticks.

Notwithstanding the above it is presently believed that there is a potential demand and a commercial market for an incense burner and storage device in accordance with the present invention.

SUMMARY OF THE INVENTION

The present invention relates generally Portable censer bag shaped like a conventional suitcase with handle, where the censer elements are housed inside the said bag. The portable censer bag is designed to mount all censer elements inside, so we can take it everywhere and use it easily.

The portable censer bag is power by electric power supply 220 v AC and also, with rechargeable battery 12 v DC through the adapter. Every piece of the censer mounted in a suitable place in the bag according to its size or height. And so, each piece is fixed while carrying the bag. There is a decoration lighting strip surround the bag which also used as indication of the charging of the battery according to light intensity. The Bag made of strong materials to withstand the shocks and coated with a layer of sponge and an artificial skin. These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention relates generally Portable censer bag shaped like a conventional suitcase with handle, where the censer elements are housed inside a special bag. The portable bag is designed to mount all censer elements inside, so we can take it everywhere and use it easily.

Figure 1:
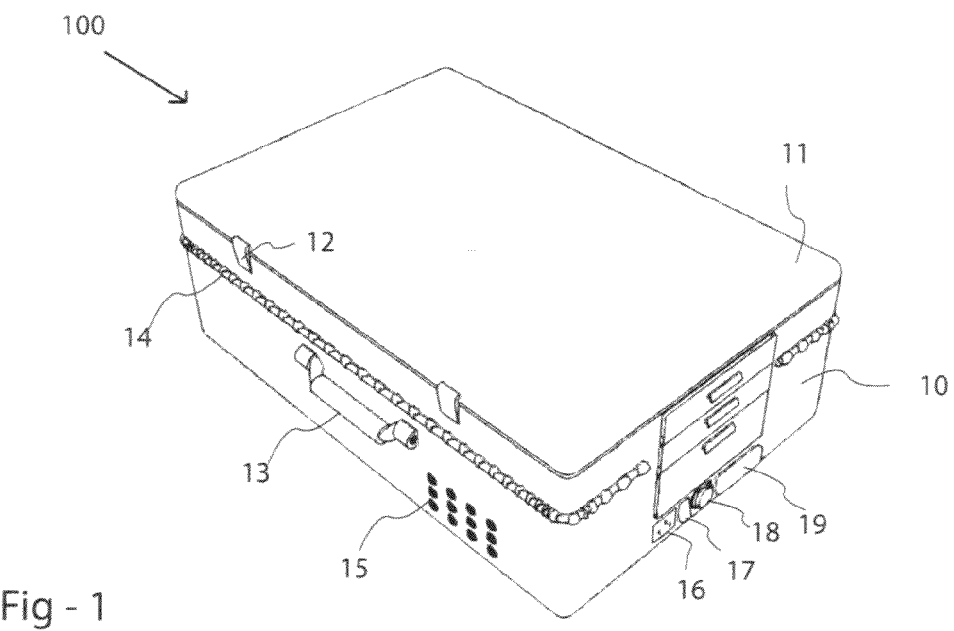
FIG. 1 is an environmental, perspective view of the portable censer bag.
Figure 2:
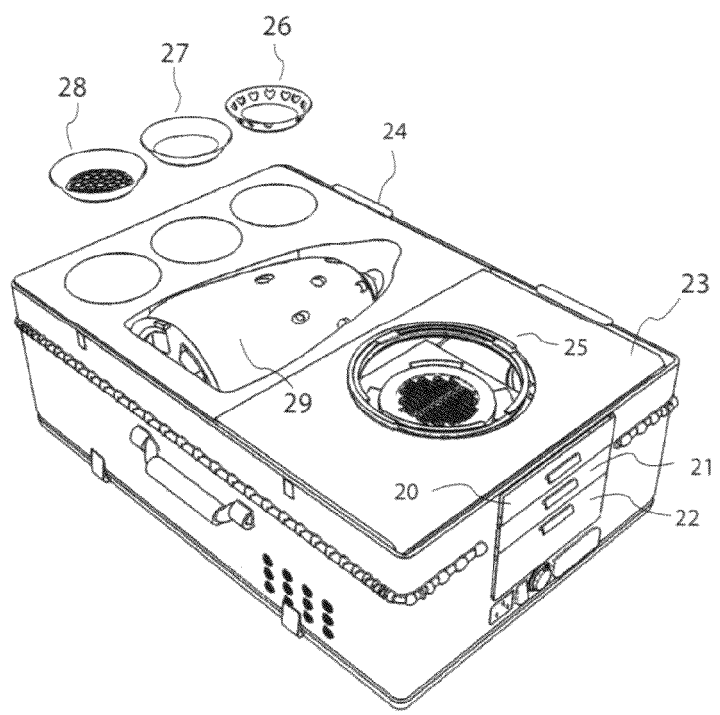
FIG. 2 is a detailed perspective view of portable censer bag.

Referring to FIGS. 1 and 2 which describe a perspective view of the portable censer bag 100 with handle 13. One end of the censer bag body 10 has three drawers 20, 21, and 22. The drawer 20 for an incense burner 33, the drawer 21 for storing cleaning materials for cleaning and washing the burner 33, and the drawer 22 for storing incense, perfumes and charcoal. The other end of the bag body 10 has three dishes 26, 27, and 28. The dish 26 is for aromatic powder dish, dish 27 for aromatic oils, and dish 28 for incense coal. The incense distribution pot 29 is stored at an indentation next to the three dishes. There is a removable bag cover 1 attached to the bag body 10 by hinges 24. The cover 11 is to close the bag by its conventional latches 12. The drawer end has a cover 13 fixed by screws not shown in figures to protect the burner 33. Lower to the drawer 22, there are electric power outlet 16, on/off switch 17, control switch 18 to control inside fan speed, and rechargeable battery 19.

Figure 3:
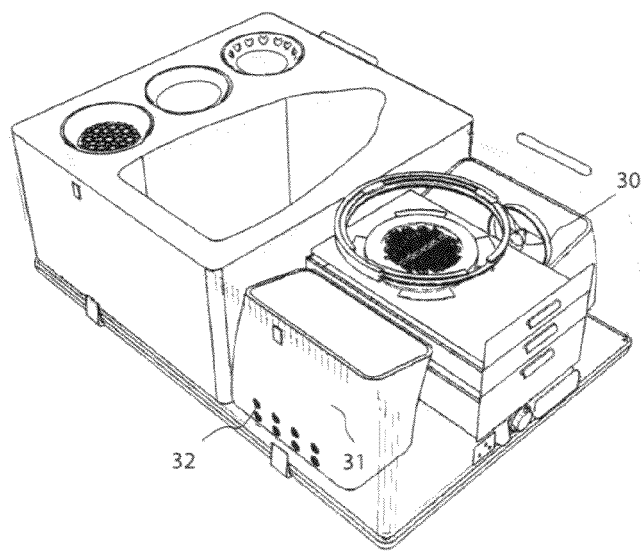
FIG. 3 is a detailed perspective view of interior design of the portable censer bag.
Figure 4:
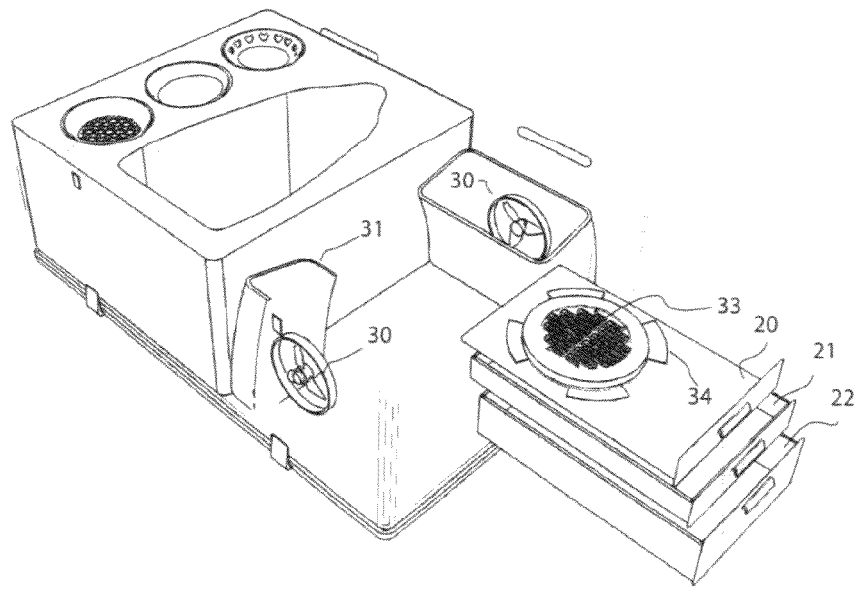
FIG. 4 is a more detailed perspective view of interior design of the portable censer bag.

To start using the censer bag, connect the electric power to the outlet 16, turn on the switch 17, the burner 33 is heated, put the suitable dish on the burner plate, mount and fix the distribution pot 29 on the incense burner 33 by lock 25, and adjust the control switch 18 to the suitable speed of the two fans 30. The two fans 30 in FIGS. 3 and 4 are located in the two edges of the drawer facing the burner 33. The two fans is used to pull the air to the bag drawer end from the holes 32 which adjacent to the bag body air entrance holes 15 then push the air direct to the burner. The duct fan frame 31 to direct air to flow towards the incense fumes to push it up in the pot 29.

Figure 5:
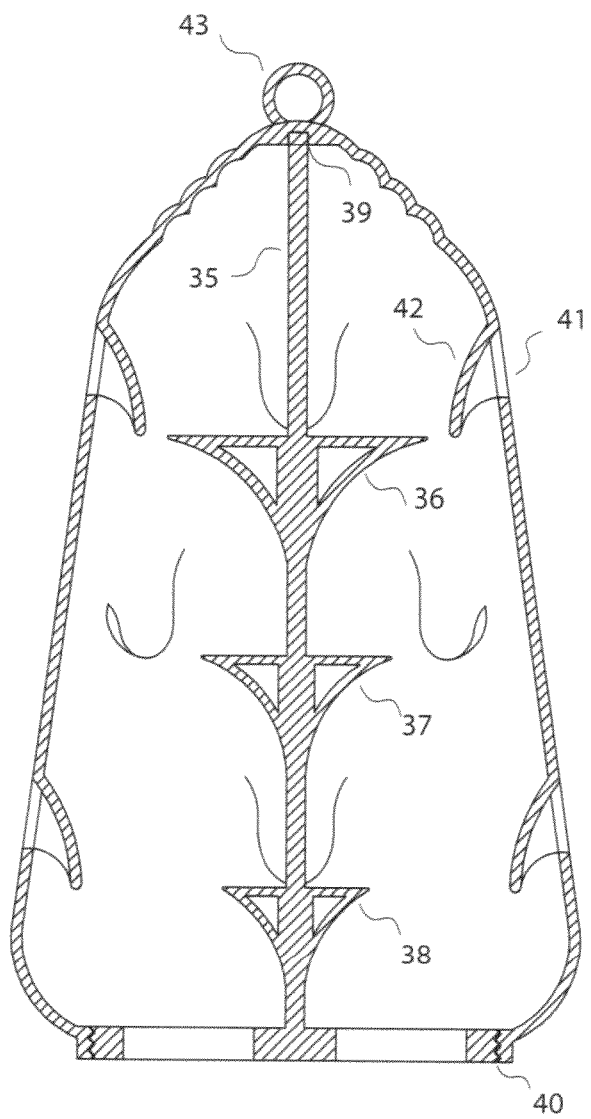
FIG. 5 is a perspective view of the distribution pot.
Figure 6:
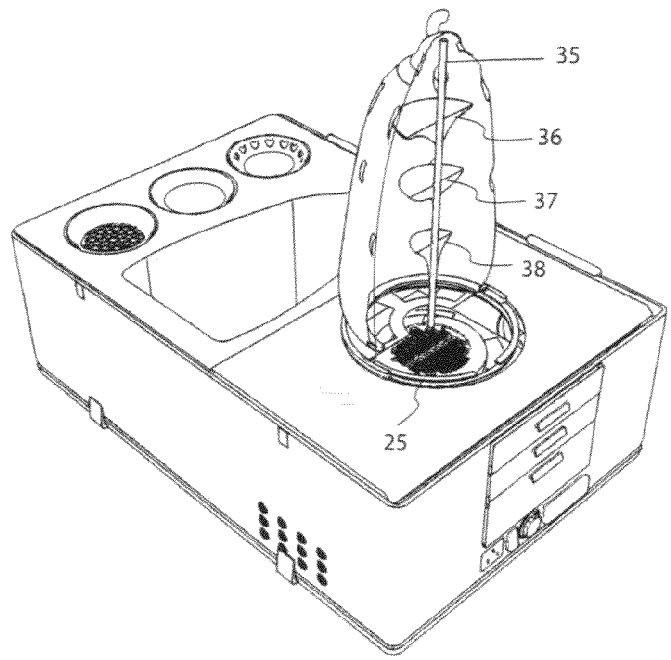
FIG. 6 is a perspective view of the portable censer bag with cross-section of the distribution pot.
Figure 7:
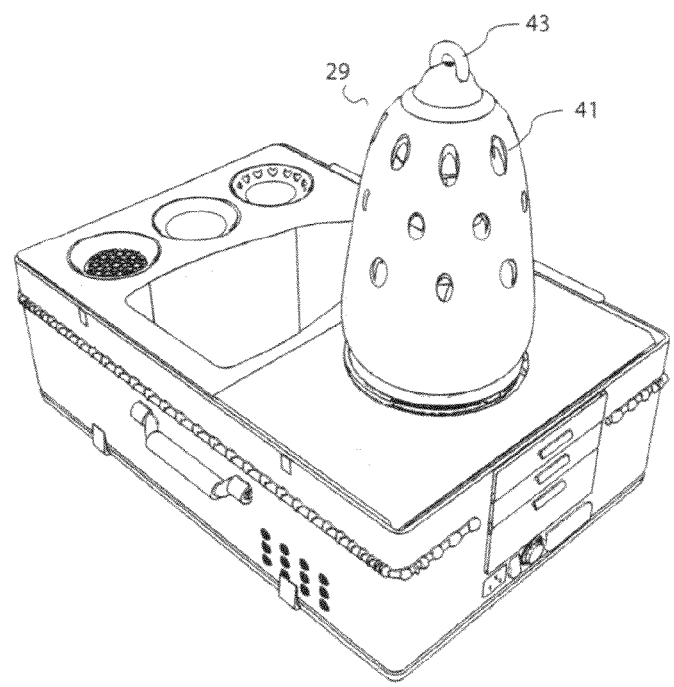
FIG. 7 is a perspective view of the portable censer bag with the distribution pot.
Figure 8:
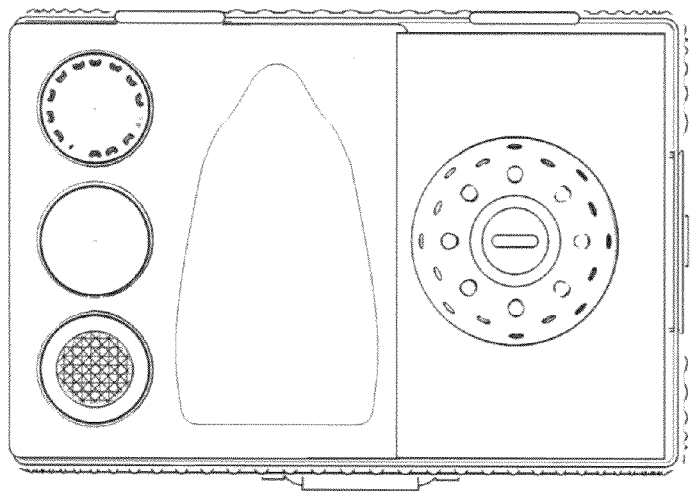
FIG. 8 is a top view of the portable censer bag.

Referring to FIGS. 5, 6, 7, the design of the pot 29 is to allow the air to rise up, where the pot 29 comprises pot base 40 fixed on the burner drawer 20 by lock 25, pot holder bar 35 in its top end 39 connected to the nut 43 to fix the pot 29 vertical on the burner, three or more distribution cones 36, 37, 38 attached to the bar 35 to direct and guide the incense fumes towards the surface pot holes 41 to direct the air in the surrounded place atmosphere to the bag, and outside pot fame 18 attached to the pot body 42 which connects the nut 43 and the support bar 35 with the pot base 40.

The ash of the incense is collected in the ash dish 34 under the burner 33. The ash can be cleaned easily by pulling the drawer and take the dish 34 out and clean it.

Figure 9:
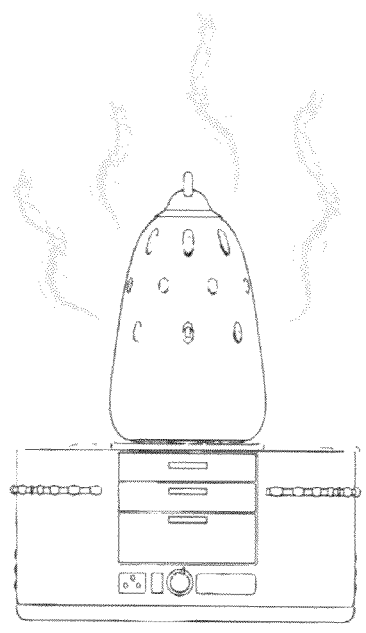
FIG. 9 is a side view of the portable censer bag.
Figure 10:
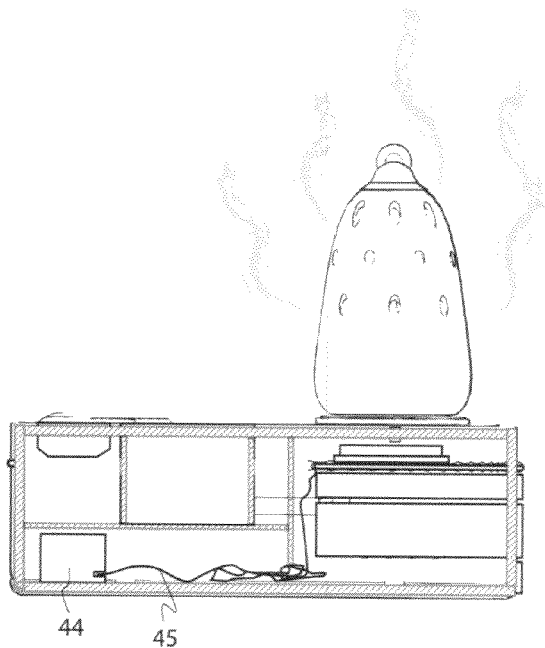
FIG. 10 is another side view of the portable censer bag.

Referring to FIGS. 9 and 10 which describe side view of the censer bag 100. In the bag 100 there is an adapter 44 to convert AC to DC 12 v which is connected to the burner 33 through a cable 45. Also, we can use timer to control the burning time not shown in figures. The portable censer bag is suitable to any place and we can carry it and use anywhere. So, we can easily, use the bag and easily clean and maintain it. The Bag made of strong materials to withstand the shocks and coated with a layer of sponge and an artificial skin. For more decoration, there lighting strip 14 surround the bag body and also used as battery charge indication.

It is to be understood that the present invention is not limited to the embodiments described above, but encompasses any and all embodiments within the scope of the following claims.

The invention claimed is:

1. A portable censer bag comprising:
a bag housing including drawers end portion, scent storage portion, and distribution pot storage portion;
said drawers end portion disposed inside the bag housing right end;
said drawers end portion including an incense burner disposed on the upper surface of the drawers end, storage drawers disposed within said drawers end portion, and two fans disposed to edges of said drawers end portion;
a panel disposed under said storage drawers, the panel disposed on the outer surface of said bag housing, said panel including an electric power outlet, an on/off switch, a control switch for controlling fan speed, and a rechargeable battery;
said scent storage portion disposed inside the bag housing left end; the scent storage portion having three dishes for storing aromatic, aromatic oil, and incense coal;
said distribution pot storage portion disposed inside the housing at an indentation next to said scent storage portion;
a distribution pot housed inside said distribution pot storage portion;
a lighting strip disposed around bag housing periphery, the lighting strip is connected to said rechargeable battery, the lighting strip is for battery charge indication;
a removable bag cover attached to the bag housing to form a lid disposed on top surface of said bag housing, latches disposed to said removable cover for closing the portable censer bag; and
a fastener for attaching said removable cover to said housing.

2. Said portable censer bag according to claim 1, wherein said drawers end portion having a cover disposed on drawers end portion surface, said cover closed the surface of the top drawer.

3. Said portable censer bag according to claim 1, further including said fans housed in said drawers end portion, said fans housed facing said incense burner, said fans including fan duct frame directing air towards incense fumes.

4. Said portable censer bag according to claim 1, wherein said distribution pot comprising:
a pot housing supported vertical by pot holder support bar; the top end of said holder support bar connected to pot housing through a nut, said pot housing including holes around said pot housing surface;
a pot base disposed to the pot housing bottom, the bottom end of said holder support bar connected to said pot base by a lock, said lock fixing said pot base over said incense burner;
more than three distribution cones attached to said holder support bar directing incense fumes outside through distribution pot surface holes.

5. Said portable censer bag according to claim 1, wherein said storage drawers including top drawer for an incense burner storage, middle drawer for cleaning materials storage, and lower drawer for perfume and charcoal storage.

6. Said portable censer bag according to claim 1, further including ash dish disposed under said incense burner for collecting an incense ash.

7. Said portable censer bag according to claim 1, wherein said bag housing includes a handle.

8. A portable censer bag comprising:
a bag housing including drawers end portion, scent storage portion, and distribution pot storage portion;
said drawers end portion disposed inside the bag housing right end;
said drawers end portion including an incense burner disposed on the upper surface of the drawers end portion, storage drawers disposed within said drawers end portion, and two fans disposed to edges of said drawers end portion;
a panel disposed under said storage drawers, the panel disposed on the outer surface of said bag housing, said panel including an electric power outlet, an on/off switch, a control switch for controlling fan speed, and a rechargeable battery;
said scent storage portion disposed inside the bag housing left end; the scent storage portion having three dishes for storing aromatic, aromatic oil, and incense coal;
said distribution pot storage portion disposed inside the housing at an indentation next to said scent storage portion;
a distribution pot housed in said distribution pot storage portion, said distribution pot including a pot housing supported vertical by pot holder support bar wherein the top end of said holder support bar connected to pot housing through a nut, holes housed in said pot housing surface, a pot base disposed to the pot housing bottom wherein the bottom end of said holder support bar connected to said pot base by a lock fixing said pot base over said incense burner, and more than three distribution cones attached to said holder support bar directing incense fumes outside through distribution pot surface holes;
a lighting strip disposed around housing periphery, the lighting strip is connected to said rechargeable battery, the lighting strip is for battery charge indication;
a removable bag cover attached to the housing to form a lid disposed on top surface of said housing, latches disposed to said removable cover for closing the portable censer bag; and
a fastener for attaching said removable cover to said housing.

9. Said portable censer bag according to claim 8, wherein said bag housing includes a handle.

* * * * *